(12) United States Patent
McGuire et al.

(10) Patent No.: US 7,559,940 B2
(45) Date of Patent: Jul. 14, 2009

(54) SURGICAL BITING PUNCH

(75) Inventors: David A. McGuire, Anchorage, AK (US); Paul A. Torrie, Marblehead, MA (US)

(73) Assignee: Smith & Nephew, Inc., Memphis, TN (US)

(*) Notice: Subject to any disclaimer, the term of this patent is extended or adjusted under 35 U.S.C. 154(b) by 453 days.

(21) Appl. No.: 10/323,578

(22) Filed: Dec. 18, 2002

(65) Prior Publication Data

US 2004/0122461 A1    Jun. 24, 2004

(51) Int. Cl.
    *A61B 17/32* (2006.01)
(52) U.S. Cl. .......................... 606/184; 606/207; 606/208
(58) Field of Classification Search ................ 606/184, 606/83, 51, 170, 52, 205–210, 174, 178, 606/167; 600/564; 30/175, 186, 188; D24/143, D24/148, 153; 81/345, 684; 269/150, 137
    See application file for complete search history.

(56) References Cited

U.S. PATENT DOCUMENTS

| 115,735 | A |   | 6/1871 | Hughes |
|---|---|---|---|---|
| 2,069,636 | A |   | 2/1937 | Wilson |
| 2,994,321 | A | * | 8/1961 | Tischler ............... 600/564 |
| 3,842,840 | A |   | 10/1974 | Schweizer |
| 4,164,225 | A |   | 8/1979 | Johnson et al. |
| 4,243,047 | A |   | 1/1981 | Olsen |
| 4,246,698 | A |   | 1/1981 | Lasner et al. |
| 4,433,687 | A |   | 2/1984 | Burke et al. |
| 4,522,206 | A |   | 6/1985 | Whipple et al. |
| 4,597,385 | A |   | 7/1986 | Watson |
| 4,712,545 | A | * | 12/1987 | Honkanen ............... 606/184 |
| 4,971,067 | A |   | 11/1990 | Bolduc et al. |
| 4,994,024 | A |   | 2/1991 | Falk |
| 5,009,661 | A |   | 4/1991 | Michelson |
| 5,203,785 | A |   | 4/1993 | Slater |
| 5,219,357 | A |   | 6/1993 | Honkanen et al. |
| 5,250,055 | A |   | 10/1993 | Moore et al. |
| 5,286,255 | A |   | 2/1994 | Weber |
| 5,387,221 | A |   | 2/1995 | Bisgaard |
| 5,389,103 | A |   | 2/1995 | Melzer et al. |
| 5,389,104 | A |   | 2/1995 | Hahnen et al. |
| 5,395,375 | A | * | 3/1995 | Turkel et al. ............... 606/83 |
| 5,395,386 | A |   | 3/1995 | Slater |
| 5,397,325 | A |   | 3/1995 | Della Badia et al. |
| 5,431,674 | A |   | 7/1995 | Basile et al. |
| 5,443,475 | A |   | 8/1995 | Auerbach et al. |
| 5,454,823 | A |   | 10/1995 | Richardson et al. |
| 5,531,755 | A |   | 7/1996 | Smith et al. |

(Continued)

FOREIGN PATENT DOCUMENTS

DE    100 56 238    5/2002

*Primary Examiner*—Anhtuan T. Nguyen
*Assistant Examiner*—Elizabeth Houston
(74) *Attorney, Agent, or Firm*—Fish & Richardson P.C.

(57) ABSTRACT

A surgical punch including an upper jaw and lower jaw that are coupled at their proximal ends. The jaws have cutting edges at their distal end configured to cut in a direction from the distal ends of the jaws towards the proximal ends of the jaws. The center of rotation of the cutting trajectory can be located above the initial cutting point of the lower jaw. The upper jaw can include a reversed slope leading edge. The jaws can be slidably coupled to each other. The coupling member can include a pin and slot to couple the movable jaw to an actuating rod.

7 Claims, 5 Drawing Sheets

U.S. PATENT DOCUMENTS

| | | |
|---|---|---|
| 5,556,407 A | 9/1996 | Wurster et al. |
| 5,569,299 A * | 10/1996 | Dill et al. .................... 606/205 |
| 5,571,131 A * | 11/1996 | Ek et al. ...................... 606/184 |
| 5,649,947 A | 7/1997 | Auerbach et al. |
| 5,683,359 A | 11/1997 | Farkas et al. |
| 5,810,883 A * | 9/1998 | Lang .......................... 606/207 |
| 5,814,054 A | 9/1998 | Kortenbach et al. |
| 5,879,371 A | 3/1999 | Gardiner et al. |
| 5,919,206 A * | 7/1999 | Gengler et al. .............. 606/205 |
| 6,019,780 A | 2/2000 | Lombardo et al. |
| 6,074,401 A | 6/2000 | Gardiner et al. |
| 6,149,658 A | 11/2000 | Gardiner et al. |
| 6,270,508 B1 * | 8/2001 | Klieman et al. ............. 606/147 |
| 6,682,548 B2 * | 1/2004 | Lang et al. .................. 606/205 |

\* cited by examiner

SURGICAL BITING PUNCH

TECHNICAL FIELD

This invention relates to medical devices, and more particularly to a surgical biting punch.

BACKGROUND

The meniscus is a C-shaped piece of fibro cartilage that is located at the peripheral aspect of the knee joint, between the femur and the tibia. There are two menisci in each knee, the medial meniscus, and the lateral meniscus. The two menisci absorb shock and spread the force of weight bearing on the joint over a larger area. They also stabilize the ligaments of the knee. The majority of the meniscus has little or no blood supply. For that reason, when damaged, the meniscus does not heal as quickly as other tissue. In addition, the meniscus begins to deteriorate over time, often developing degenerative tears.

Typically, when the meniscus is damaged, the torn piece begins to move abnormally within the joint. Because the space between the bones of the joint is very small, as the abnormally mobile piece of meniscal tissue moves, it may become caught between the femur and tibia. Usually this situation requires that the torn piece be removed. A surgeon can use an instrument, often referred to as a "biter" to remove the tear. The instrument is referred to as a biter because its cutting edges are typically in the shape of a semi-circle or a square and part of jaws that open and close. The cutting edges therefore cut a piece of the meniscus in the shape of a semicircle or a square when the jaws are closed, giving the appearance of taking a bite.

SUMMARY

In one aspect there is a surgical punch including a first jaw having a first cutting edge, a second jaw having a second cutting edge and a coupling member. The coupling member is disposed at proximal end portions of the first and second cutting edges and configured to bring the first and second jaws towards each other when actuated. Further, the jaws are configured to cause cutting from distal ends towards proximal ends of the jaws when the jaws are brought towards each other.

In other examples, the surgical punch can include one or more of the following features. A portion of the first cutting edge can be disposed distal to the second cutting edge. The first cutting edge can further include a first distal portion that is closest to the second jaw at a distal end of the first distal portion and farthest from the second jaw at a proximal end of the first distal portion when the first jaw is parallel to the second jaw. The second cutting edge can further include a second distal portion that is closest to the first jaw at a distal end of the second distal portion and farthest from the first jaw at a proximal end of the second distal portion when the first jaw is parallel to the second jaw.

The surgical punch can also include a projected point of rotation of the cutting located outside of the coupling member. The first jaw can be an upper jaw and the second jaw can be a lower jaw, and the surgical punch can further include a projected point of rotation of the cutting that is located above an initial cutting point of the second cutting edge. The first jaw can further include a leading edge having a reverse slope. The leading edge can be configured to guide the first jaw between a meniscus and a femoral chondyle associated with the meniscus.

The coupling member can include a pivot pin. The coupling member can include a pinless hinge, wherein the first jaw is slidably coupled to the second jaw. The coupling member can include one of an arcuate flange and an arcuate groove.

The surgical punch can be configured where the coupling member comprises the following:

one of the jaws comprising at least one first arcuate flange and the other of the jaws comprising at least one first arcuate groove, the at least one first arcuate flange being slidably disposed in the at least one first arcuate groove so as to pivotally couple the first jaw to the second jaw, whereby the first jaw is capable of pivotal movement towards and away from the second jaw, with the at least one first arcuate flange and the at least one first arcuate groove having a first center of curvature that is fixed in position relative to the second jaw when the at least one first arcuate flange is disposed in the at least one first arcuate groove, and one of the first jaw and an actuating member comprising at least one second arcuate flange and the other of the first jaw and the actuating member comprising at least one second arcuate groove, the at least one second arcuate flange being slidably disposed in the at least one second arcuate groove so as to pivotally couple the actuating member to the first jaw, with the at least one second arcuate flange and the at least one second arcuate groove having a second center of curvature that is fixed in position relative to the actuating member and is not fixed in position relative to the second jaw when the at least one second arcuate flange is disposed in the at least one second arcuate groove, and one of the centers of curvature is displaced laterally from the second stationary jaw and the actuating member, whereby (a) when the actuating member is actuated in a first direction relative to the second jaw, the first jaw will open away from the second jaw, and (b) when the actuating member is moved in a second opposite direction relative to the second jaw, the first jaw will close towards the second jaw, the first and second jaws being arranged so that body tissue located between the first and second jaws may be severed in a punching motion as the jaws are opened and closed relative to one another by actuating the actuating member.

The coupling member can also include a pin coupled to the first jaw and an actuating member and a slot to receive the pin, where the slot is configured to allow free passage of the pin as the actuating member is actuated. The slot can include an arcuate portion. The first jaw can be a movable jaw and the second jaw can be a stationary jaw. The first jaw can be a stationary jaw and the second jaw can be a movable jaw.

In another aspect, there is a surgical punch that includes a first movable jaw, a second stationary jaw and a coupling member. The first movable jaw has a first cutting edge and a leading edge including a reverse slope. The second stationary jaw has a second cutting edge disposed proximal to a portion of the first cutting edge. The coupling member slidably couples the first jaw to the second jaw. The coupling member is disposed at proximal end portions of the first and second cutting edges, and configured to bring the first and second jaws towards each other when actuated. The jaws are configured to cause cutting from distal ends towards proximal ends of the jaws when the jaws are brought towards each other.

In another aspect, there is a surgical punch including an actuating rod, a fist jaw, a second jaw, a pin, and a coupling member. The first jaw has a first cutting edge. The pin movably couples the first jaw to the actuating rod. The second jaw has a second cutting edge and a slot configured to allow free passage of the pin as the actuating member is actuated. The coupling member is disposed at proximal end portions of the first and second cutting edges. The coupling member includes a flange and a groove configured to bring the first and second jaws towards each other when actuated.

In another aspect, there is a surgical punch including a first jaw, a second jaw and a coupling member. The upper jaw has a first cutting edge. The lower jaw has a second cutting edge. The coupling member couples the upper jaw to the lower jaw. The coupling member includes a center of rotation, where the center of rotation is configured to cause a predefined vertical cut in target tissue. In one example, the predefined cut is more distal, with respect to the surgical punch, at an end of the tissue closest to the upper jaw than at an end of the tissue closest to the lower jaw. The surgical punch can also include one or more of the features listed above.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
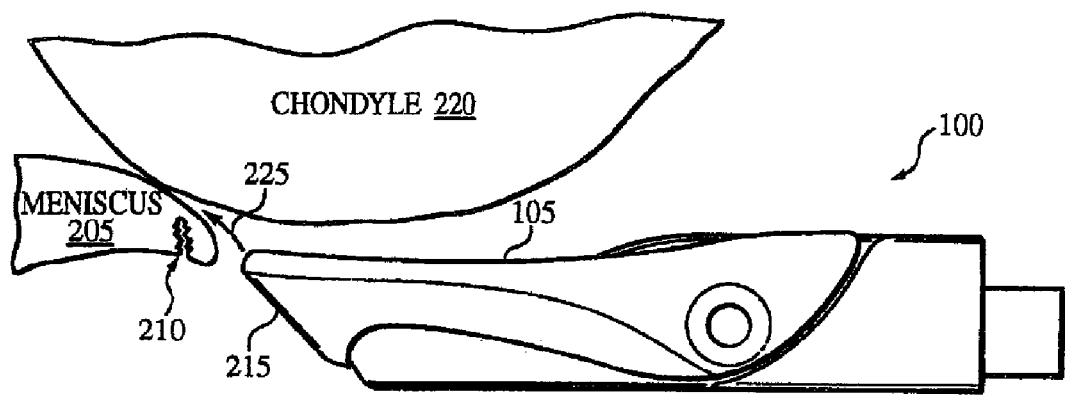
FIG. 1 is a side view of a surgical punch with closed jaws.

FIG. 1 illustrates a surgical punch 100 for use in repairing a meniscus 205 having a tear 210. Surgical punch 100 includes a moveable upper jaw 105 having a sloped leading edge 215 with a reverse slope. In other words, the slope of leading edge 215 from the distal end to the proximal end is negative. This reverse sloped leading edge 215 enables a surgeon to guide the distal end of surgical punch 100 between meniscus 205 and a femoral chondyle 220, as indicated by arrow 225. Leading edge 215 also enables a surgeon to easily position upper jaw 105 above meniscus 205 for a cutting procedure.

Figure 2:
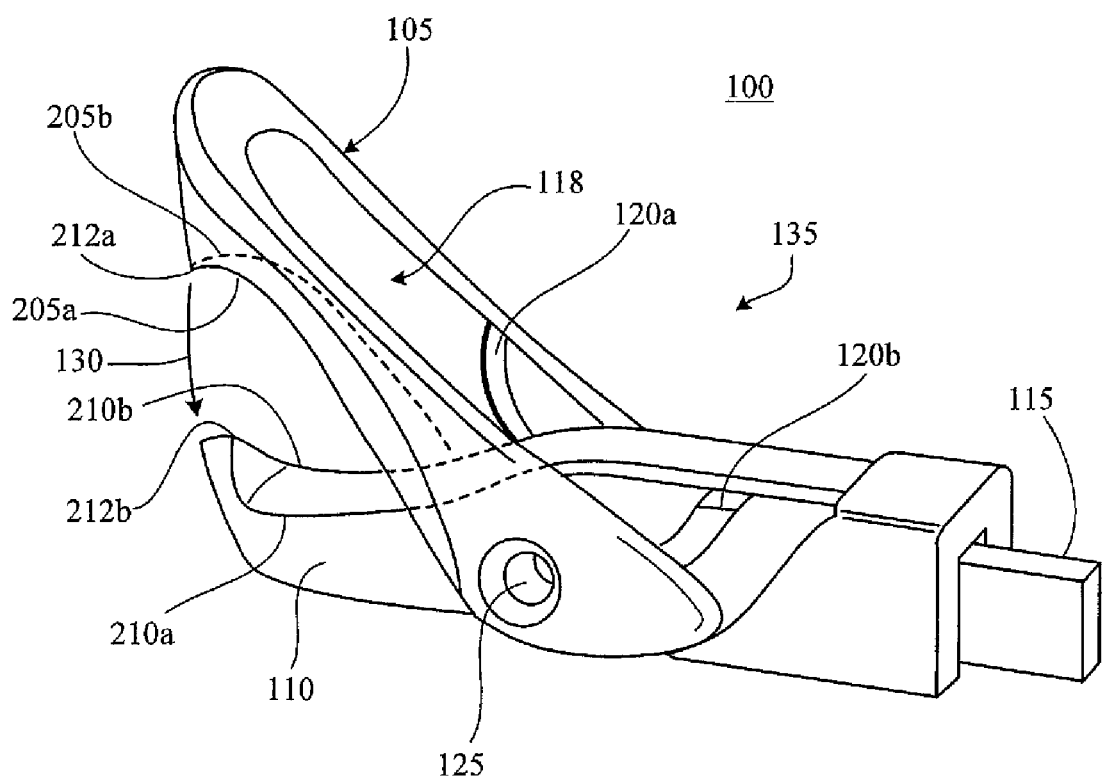
FIG. 2 is a perspective view of the surgical punch.

Referring to FIG 2, surgical punch 100 also includes a stationary lower jaw 110 and an actuating rod 115. Actuating rod 115 is connected to handles (not shown), such as scissor-like handles typically seen on biting punches and other similar surgical instruments. The handles move actuating rod 115 towards and away from moveable jaw 105 and stationary jaw 110. During use, when actuating rod 115 is moved away from the distal end of the punch, jaws 105 and 110 move toward each other (i.e., close). As a surgeon moves actuating rod 115 toward the distal end of the punch, upper jaw 105 moves away from lower jaw 110 (i.e., open). When viewed from above, upper jaw 105 is "U" shaped and has an opening 118. This opening 118 allows a surgeon to view the portion of the target tissue that will be cut by surgical punch 100.

Figure 5:
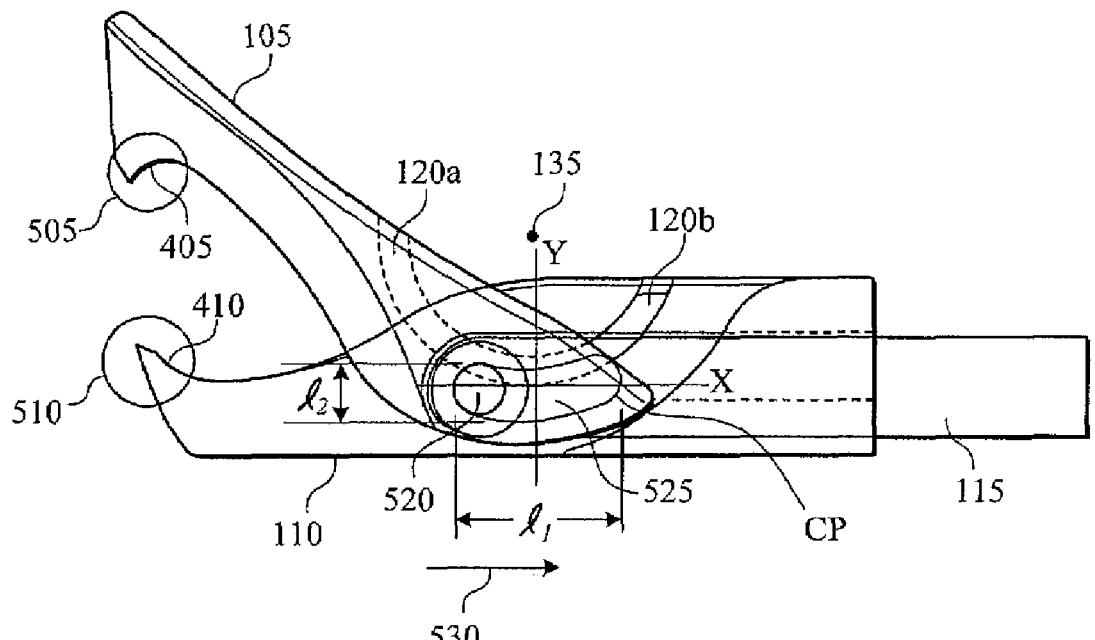
FIG. 5 is a transparent side view of the surgical punch.

To enable upper jaw 105 to move, surgical punch 100 includes a sliding coupling mechanism 120. Sliding mechanism 120 has a groove 120a, in the shape of a semi-circle, located on the inner walls of upper jaw 105. Sliding mechanism 120 also has a corresponding flange 120b, also in the shape of a semi-circle, located on the outer walls of lower jaw 110. As upper jaw 105 moves, groove 120a slides along and is guided by flange 120b. To connect upper jaw 105 to actuating rod 115, feature 125 includes a pin 520 (FIG. 5). The pin 520 extends from one side of upper jaw 105, through actuating rod 115, to the other side of upper jaw 105. To accommodate this pin 520, lower jaw 110 includes a slot 525 (FIG. 5) so that there is no obstructing material as the pin 520 moves with upper jaw 105 as actuating rod 115 moves.

The pin 520 at feature 125 is not a pivot pin about which upper jaw 105 rotates. Unlike the alternative example described below, sliding mechanism 120 does not include a pivot pin. Because upper jaw 105 slides, the cutting trajectory 130 has a projected center of rotation 135 that is outside of and above the jaws 105 and 110. As described in more detail below, having a projected center of rotation 135 above the initial cutting point of lower jaw 110 allows cutting by upper jaw 105, along trajectory 130, to be more distal when jaws 105 and 110 are furthest apart (as shown) than when jaws 105 and 110 are closed.

Figure 3:
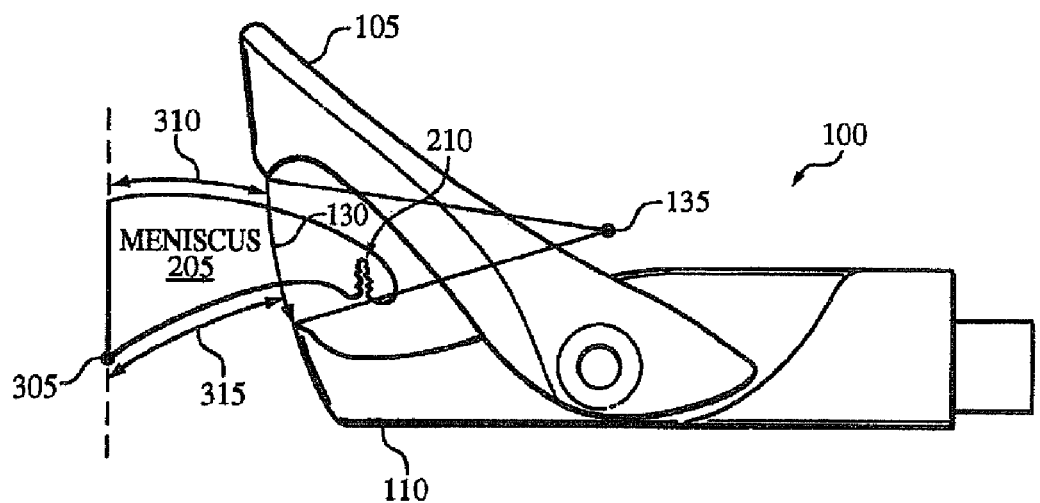
FIG. 3 is a side view of the surgical punch with open jaws.

FIG. 3 illustrates jaws 105 and 110 in an open position around meniscus 205, ready to begin a cutting procedure. Meniscus 205 attaches at point 305 to the tibial plateau. The meniscus 205 can also attach along the vertical rear edge (from point 305 and up). Arrow 310 represents the distance along the top of meniscus 205 from the plane of attachment to the cut, at the cutting trajectory 130, made by surgical punch 100. Similarly, arrow 315 represents the distance along the bottom of meniscus 205 from the plane of attachment to the cut, at the cutting trajectory 130, made by surgical punch 100. The larger the difference between distance 315 and distance 310, the more stable the remaining meniscus will be. As described above, the projected center of rotation 135 for cutting trajectory 130 is above lower jaw 110 for surgical punch 100. This means that the cutting trajectory 130 is more distal at the top of meniscus 205 than at the bottom of meniscus 205. The higher the projected center of rotation 135 is above the lower jaw 110, the more distal the cutting trajectory 130 will be at the top of meniscus 205, as compared with the bottom of meniscus 205. In other words, the higher the projected center of rotation 135 is, the greater the difference between distances 310 and 315.

Figure 4A:
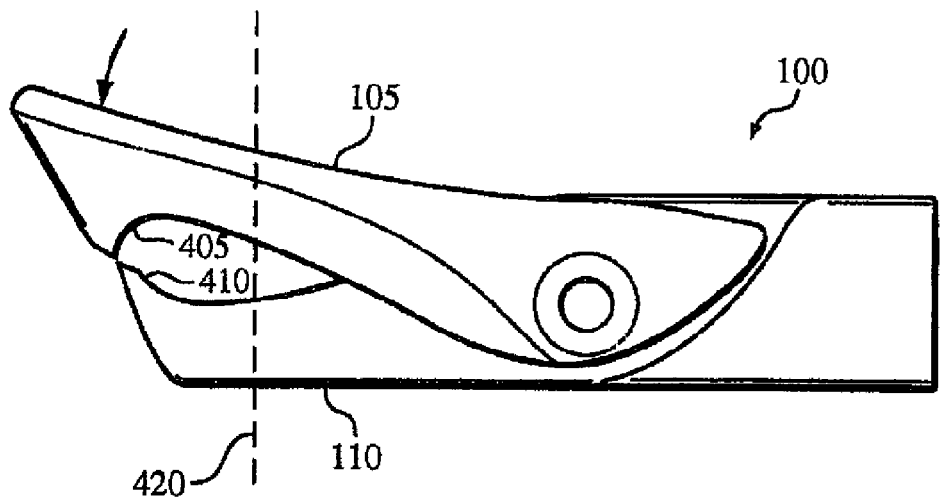
FIGS. 4A and 4B are side views of the surgical punch with jaws closing.
Figure 4B:
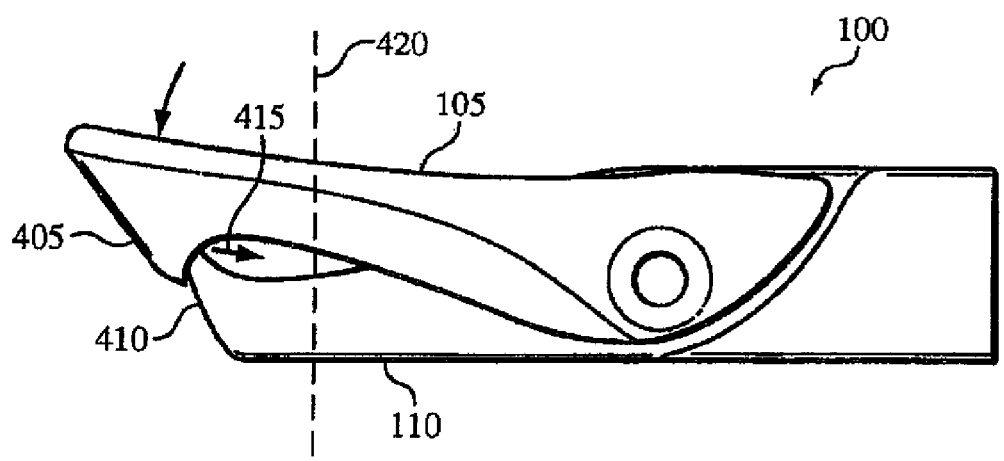

FIGS. 4A and 4B illustrate how surgical punch 100 cuts tissue during a cutting procedure, from the punch's distal end towards its proximal end. Referring to FIG. 4A, as jaws 105 and 110 move towards each other, cutting edge 405 of upper jaw 105 (formed by a pair of longitudinally extending cutting edges 205a, 205b shown in FIG. 2) meets cutting edge 410 of lower jaw 110 (formed by a pair of longitudinally extending cutting edges 210a, 210b shown in FIG. 2). As shown in FIG. 2, each pair of longitudinally extending cutting edges 205a, 205b and 210a, 210b converge to form a single pointed tip 212a, 212b, respectively. When cutting edges 405 and 410 first meet, they meet at the distal end of punch 100, at the most distal point of lower jaw 110. Because cutting edges 405 and 410 are configured into sharp, pointed edges at the first point of contact with the tissue, cutting edges 405 and 410 initially pierce the meniscus 205 (FIG. 3) at a location that is distal, with respect to punch 100, to tear 210 (FIG. 3).

Referring to FIG. 4B, as jaws 105 and 110 continue to close, the distal ends of cutting edges 405 and 410 start to overlap each other with the pair of cutting edges 205a, 205b of upper jaw 105 extending distally of lower jaw 110. As cutting edges 405 and 410 overlap, the overlap at the distal ends of jaws 105 and 110 starts at the distal most point of cutting edges 405 and 410 and moves proximally, as indicated by arrow 415. This also means that cutting edges 405 and 410 cut tissue in a direction from the distal end of punch 100 toward the proximal end, as indicated by arrow 415. It may be worth noting that the proximal ends of jaws 105 and 110 also overlap. As jaws 105 and 110 close, the overlap at the proximal ends of jaws 105 and 110 occurs in a direction from the proximal end towards the distal end, the opposite direction of arrow 415. Arbitrarily placed dashed line 420 helps illustrate this. The portions of jaws 105 and 110 that are distal to dashed line 420 have cutting edges 405 and 410 that overlap each other in a direction that is distal to proximal, as indicated by arrow 415. The portions of jaws 105 and 110 that are proximal to dashed line 420 overlap each other in a direction that is proximal to distal, the opposite of arrow 415.

FIG. 5 illustrates the geometry of a distal portion 505 of cutting edge 405 and a distal portion 510 of cutting edge 410. Distal portion 505 has a sharp, positive, and changing slope. The positive slope on upper jaw 105 ensures that as jaws 105 and 110 close, the overlap of cutting edges 405 and 410 progresses in a direction that is distal to proximal, with respect to jaws 105 and 110. Distal portion 510 has a sharp, negative, and changing slope. Similarly, the negative slope on lower jaw 110 ensures that as jaws 105 and 110 close, the overlap of cutting edges 405 and 410 progresses in a direction that is distal to proximal, with respect to jaws 105 and 110. To maintain the progression of the overlap in a direction that is distal to proximal, the slopes can be configured based on projected center of rotation 135. As illustrated in FIG. 1, portions 505 and 510 are configured so that they do not protrude when the jaws 105 and 110 are fully closed. In other words portion 505 does not go beyond the bottom of lower jaw 110 and similarly, portion 510 does not go beyond the top of upper jaw 105.

Referring back to FIG. 5, also illustrated is a transparent view of surgical punch 100 exposing, in particular, the sliding mechanism 120, that couples upper jaw 105 to lower jaw 110, and the pin 520 and slot 525, that couples upper jaw 105 to actuating rod 115. The slot 525 has a closed plane, CP, bounded by the lower jaw 110, and the length, $l_1$, of the closed plane along a proximal to distal axis, X, of the surgical punch 100 is different from the length, $l_2$, of the closed plane along a second axis, Y, transverse to the proximal to distal axis of the surgical punch 100. As described above, pin 525 is connected to both upper jaw 105 and actuating rod 115. As a surgeon actuates actuating rod 115, causing it to move in a proximal direction as indicated by arrow 530, pin 520 moves along slot 525, pulling upper jaw 105 in a proximal direction. As upper jaw 105 moves, its curved groove 120a rides along flange 120b, which forms a semi-circular track. Moving along semi-circular flange 1 20b causes upper jaw 105 to rotate around projected center of rotation 135. To accommodate this rotation, slot 525 is also curved, having the same projected center of rotation 135.

Figure 6:
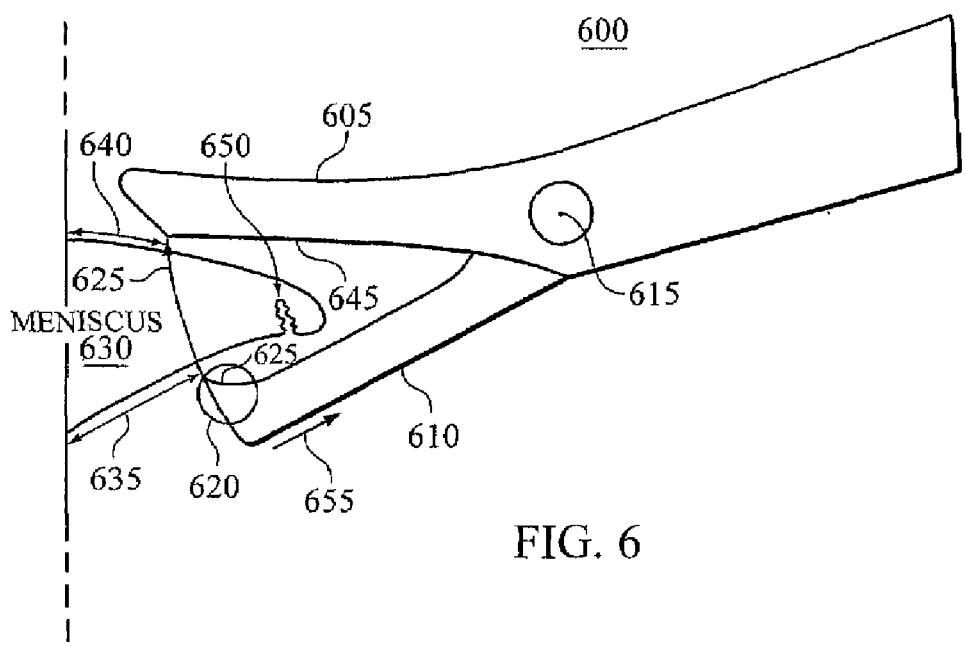
FIG. 6 is a side view of another example of a surgical punch.

FIG 6 illustrates another example of a biting punch 600. Biting punch 600 includes a stationary upper jaw 605 and a moveable lower jaw 610 attached with a coupling pin 615. Because the coupling between the jaws is not a sliding mechanism, the center of rotation for lower jaw 610 is at pin 615. This center of rotation 615 is above the initial cutting point of lower jaw 610, which is the distal most point of distal portion 620 of cutting edge 625. Having the center of rotation 615 above the initial cutting point of lower jaw 610 causes the cutting trajectory 665 to be more proximal when jaws 605 and 610 are open than when jaws 605 and 610 are closed. This ensures that the cut at the bottom of meniscus 630 is more proximal than the cut at the top of meniscus 630. In other words, distance 635 is greater than distance 640, resulting in a more stable meniscus rim after the surgeon completes the cutting procedure.

Distal portion 620 of cutting edge 625 has a sharp, negative slope from the distal end to its proximal end. Cutting edge 645 is simply flat across upper jaw 605. In another example, upper jaw 605 can have a sharp point similar to upper jaw 105. This configuration causes cutting edge 625 to initially pierce the meniscus 630 at the first point of contact with the tissue, at a location that is distal, with respect to punch 600, to tear 650. As jaws 605 and 610 continue to close, the distal end of cutting edge 625 starts to overlap cutting edge 645. As cutting edge 625 overlaps, this overlap, at the distal ends of jaws 605 and 610 starts at the distal most point of cutting edge 625 and moves proximally, as indicated by arrow 655. This also means that cutting edges 625 and 645 can cut tissue in a direction from the distal end of punch 600 toward the proximal end, as indicated by arrow 655.

Figure 7:
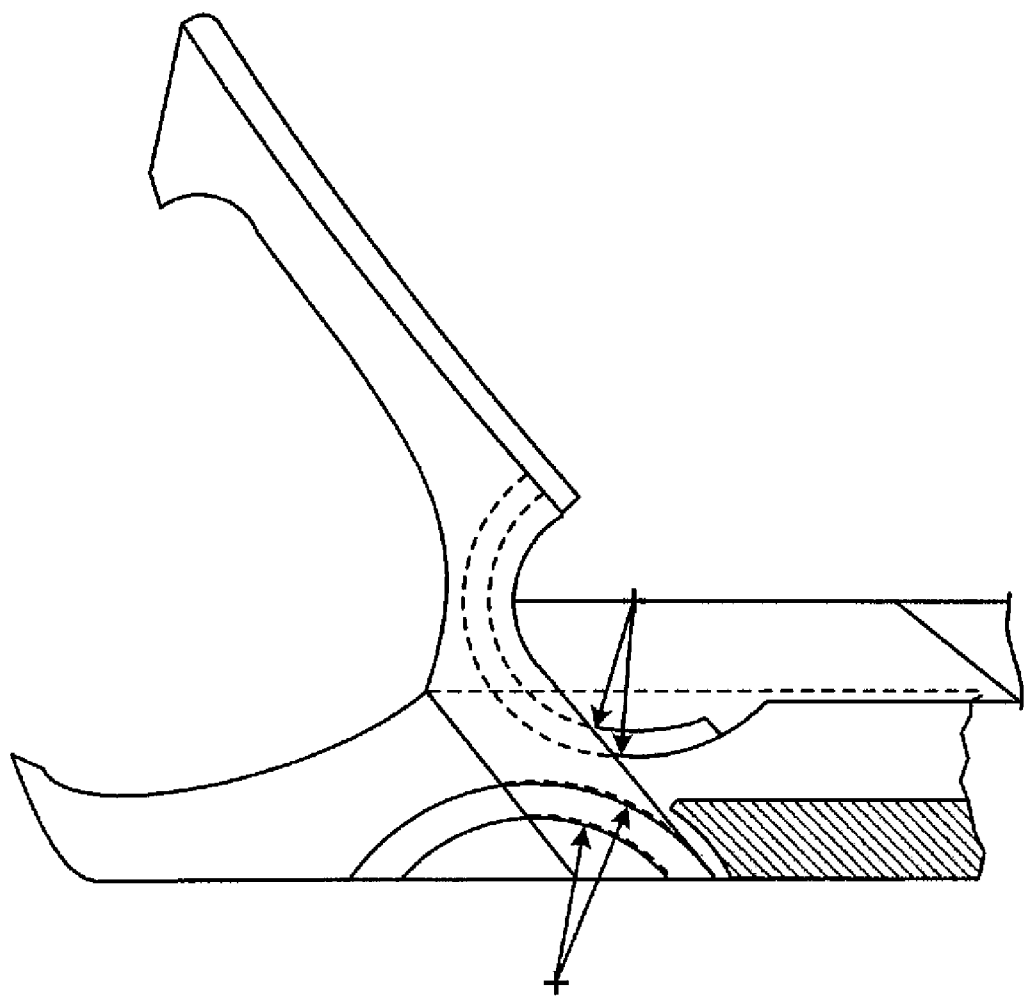
FIG. 7 is a side view of an alternative implementation of a surgical punch.

A number of embodiments of the invention have been described. Nevertheless, it will be understood that various modifications may be made without departing from the spirit and scope of the invention. For example only and not to limit other alternatives, the grooves on the upper jaw and the flanges on the lower jaw can be reversed so that the upper jaw has flanges and the lower jaw has grooves. The "U" shape of the upper jaw can be different geometries, such as square. The actuating rod can be cylindrical. The coupling mechanism can be completely pinless (e.g., no pin 520) and include a second groove/flange pair for actuation, such as the one shown in FIG. 7 and described in U.S. Pat. No. 4,712,545, incorporated herein by reference. A surgeon, or any medical personnel, can use the surgical punch on tissue other than a meniscus. Accordingly, other embodiments are within the scope of the following claims.

What is claimed is:

1. A surgical punch comprising:
an actuating rod;
a first jaw having a first cutting edge;
a second jaw having a second cutting edge, the surgical punch having a proximal region and a distal region, the first and second jaws being located at the distal region; and
a coupling member coupling the actuating rod, the first jaw, and the second jaw, the coupling member including a non-circular, arcuate flange and an arcuate groove configured to bring the first and second jaws towards each other when actuated, the coupling member further including a pin movably coupling the first jaw to the actuating rod,
wherein the second jaw defines a slot having a closed plane bounded by the second jaw, the slot configured to allow arcuate movement of the pin between proximal to distal ends of the slot as the actuating rod is actuated, the length of the closed plane along a proximal to distal axis of the surgical punch being different from the length of the closed plane along a second axis transverse to the proximal to distal axis.

2. The surgical punch of claim 1 wherein the jaws are configured to cause cutting from distal ends towards proximal ends of the jaws when the jaws are brought towards each other.

3. The surgical punch of claim 1 further comprising a projected point of rotation of a cutting trajectory of the first cutting edge located outside of the coupling member.

4. The surgical punch of claim 1 wherein the first jaw is an upper jaw and the second jaw is a lower jaw, the surgical punch further comprising a projected point of rotation of a cutting trajectory of the first cutting edge located above an initial cutting point of the second cutting edge.

5. The surgical punch of claim 1 wherein the first jaw further comprises a tapered, leading edge.

6. The surgical punch of claim 5 wherein the leading edge is further configured to guide the first jaw between a meniscus and a femoral chondyle associated with the meniscus.

7. The surgical punch of claim 1 wherein the first jaw is a movable jaw and the second jaw is a stationary jaw.

* * * * *

UNITED STATES PATENT AND TRADEMARK OFFICE
CERTIFICATE OF CORRECTION

PATENT NO. : 7,559,940 B2  Page 1 of 1
APPLICATION NO. : 10/323578
DATED : July 14, 2009
INVENTOR(S) : David A. McGuire et al.

It is certified that error appears in the above-identified patent and that said Letters Patent is hereby corrected as shown below:

Col. 4, Line 5 of Issued Patent – Delete "upperjaw" and insert -- upper jaw --, therefor.

Col. 4, Line 6 of Issued Patent – Delete "upperjaw" and insert -- upper jaw --, therefor.

Col. 5, Line 37 of Issued Patent – Delete "upperjaw" and insert -- upper jaw --, therefor.

Col. 5, Line 38 of Issued Patent – Delete "upperjaw" and insert -- upper jaw --, therefor.

Col. 5, Line 51 of Issued Patent – Delete "1 20b" and insert -- 120b --, therefor.

Signed and Sealed this

Twenty-second Day of December, 2009

David J. Kappos
*Director of the United States Patent and Trademark Office*